United States Patent [19]

Weissman

[11] 4,202,101
[45] May 13, 1980

[54] DENTAL ANCHOR AND A PLASTIC SHANK FOR HOLDING SAME

[75] Inventor: Bernard Weissman, New York, N.Y.

[73] Assignee: Ipco Hospital Supply Corporation, White Plains, N.Y.

[21] Appl. No.: 887,173

[22] Filed: Mar. 16, 1978

[51] Int. Cl.² ............................................. A61K 5/02
[52] U.S. Cl. ................................................... 433/225
[58] Field of Search .................. 32/15, 7, 6; 408/226; 145/50 B, 50 D, 50 R

[56] References Cited

U.S. PATENT DOCUMENTS

| 2,338,437 | 1/1944 | Karlstrom | 32/27 |
| 2,522,217 | 9/1950 | Fischer et al. | 145/50 R |
| 2,899,996 | 8/1959 | Stockman | 145/50 R |
| 3,395,455 | 8/1968 | Overby et al. | 128/92 R |
| 3,499,222 | 3/1970 | Linkow et al. | 32/10 A |
| 3,675,328 | 7/1972 | Weissman | 32/15 |
| 3,675,329 | 7/1972 | Weissman | 32/15 |
| 3,874,081 | 4/1975 | Franklin et al. | 32/15 |
| 3,982,846 | 9/1976 | Steinbach | 408/222 |

*Primary Examiner*—Louis G. Mancene
*Assistant Examiner*—John J. Wilson
*Attorney, Agent, or Firm*—Friedman, Goodman & Teitelbaum

[57] ABSTRACT

A plastic shank holding a metal dental anchor therein is disclosed, wherein the dental anchor is for anchoring a superstructure to a tooth. The dental anchor includes at least one threaded section and one manipulating end section joined together by a frangible portion so that the sections can be severed. The shank includes an opening for receiving the manipulating end section of the dental anchor in a force-fit connection therebetween, where the manipulating end section includes torque transferring wing portions for permitting the shank to pivot relative to the dental anchor when the dental anchor is being threaded into a channel in a tooth. A plastic hand driver is provided for receiving the shank therein, where the hand driver includes an abutment portion for rotating the shank, and projections for providing a snapped-in connection between the shank and the hand driver to permit a pivotal relationship therebetween while releasably retaining the shank within the hand driver.

30 Claims, 25 Drawing Figures

DENTAL ANCHOR AND A PLASTIC SHANK FOR HOLDING SAME

BACKGROUND OF THE INVENTION

The present invention relates to dentistry in general, and more particularly to an apparatus for building super-structures on broken or undermined dentition, the apparatus being a dental anchor, a shank for holding the dental anchor, and a hand driver for holding and turning the shank.

Prior art apparatus for anchoring a superstructure to an understructure of a tooth requires drilling a number of channels into the tooth or understructure, where dental anchors are then inserted into the channels and are allowed to protrude above the understructure so that the protruding portions thereof serve as means for anchoring the superstructure. It is noted, that these dental anchors are extremely small, being approximately 0.03" in diameter and approximately 0.2" in length.

Because of the relatively small size of the dental anchors, and because of the limited working areas, a chuck attachment or a coupling tool is used by the dentist to hold the dental anchor when being inserted into the channels. Such chuck attachments or coupling tools are disclosed in my U.S. Pat. No. 3,434,209; No. 3,675,329 and No. 4,053,982, to which reference may be made.

It is noted, that each of the dental anchors of my above mentioned patents must be threaded into a channel already formed in the tooth. Accordingly, care must be taken to insure that the longitudinal axis of the dental anchor is in alignment with the longitudinal axis of the channel, so that the dental anchor does not form its own hole in the tooth, which may lead to the tooth fracturing. Due to the size of the dental anchor, as mentioned above, this task of alignment is rather difficult, and depends upon the skill of the dentist. Furthermore, the prior art does not disclose a hand driver for the chuck attachment or coupling tool which permits a pivotal relationship therebetween.

SUMMARY OF THE INVENTION

Accordingly, it is an object of the present invention to provide means for building a superstructure on broken or undermined dentition.

Another object of the present invention is to provide means for holding a dental anchor used for anchoring a superstructure to an understructure of a tooth, where the holding means permit a pivotal relationship therebetween.

A further object of the present invention is to provide a plastic shank for holding metal dental anchors therein.

Yet another object of the present invention is to provide the above mentioned dental anchor with torque transferring wing portions for permitting the shank to pivot relative to the dental anchor when the dental anchor is being threaded into a channel in a tooth.

And yet another object of the present invention is to provide a plastic hand driver for receiving the above mentioned shank therein, where the hand driver releasably retains the shank for rotation thereof while permitting a pivotal relationship therebetween.

An added object of the present invention is to provide a highly novel, efficient and long lasting dental anchor for building superstructures on broken or undermined dentition, where the dental anchor is provided with wing portions which are twisted relative to each other to provide a force-fit in a plastic shank while permitting a pivotal relationship therebetween.

These objects are achieved in accordance with the present invention, wherein each plastic shank holds a metal dental anchor therein, the dental anchor being constructed for anchoring a superstructure to a tooth. The dental anchor includes at least one threaded section and one manipulating end section joined together by a frangible portion so that these sections can be severed once the dental anchor is threaded into a channel in the tooth. The shank includes an opening for receiving the manipulating end section of the dental anchor in a force-fit connection therebetween.

The manipulating end section includes torque transferring wing means for permitting the shank to pivot relative to the dental anchor when the dental anchor is being threaded into the channel. The wing means includes a pair of wing portions twisted relative to each other, being received in a diamond shaped portion of the shank opening. Preferably, the longitudinal edges of the wing portions are arcuate so that the wing portions are widest across their centers to provide a pivoting action thereof with respect to the shank.

Additionally, a plastic hand driver is provided for receiving the shank therein, the hand driver including abutment means for rotating the shank, and projecting means providing a snapped-in connection for releasably retaining the shank within the hand driver, where the snapped-in connection permits a pivotal relationship between the shank and the hand driver when the dental anchor is being threaded into the channel in the tooth. Thus, after the threaded sections have been sufficiently threaded into their respective channels, the manipulating end portion is snapped off or severed, whereby the shank containing the several manipulating end portion may be released from the hand driver and disposed of, the plastic shank being of the throw-away type. It should be noted, that the resiliency and flexibility of the plastic shank permits a slight bending thereof to also allow for the alignment of the dental anchor with the pre-formed channel in the tooth.

BRIEF DESCRIPTION OF THE DRAWINGS

With the above and additional objects and advantages in view, as will hereinafter appear, this invention comprises the devices, combinations and arrangements of parts hereinafter described by way of example and illustrated in the accompanying drawings of a preferred embodiment in which.

In the various figures of the drawings like reference characters designate like parts.

DETAILED DESCRIPTION OF THE PREFERRED EMBODIMENTS

Figure 1:
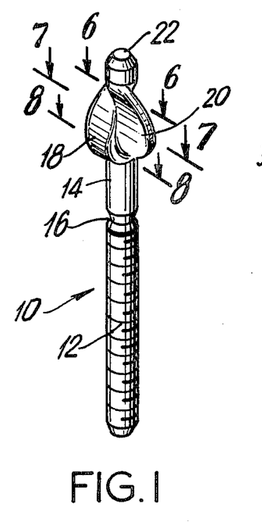
FIG. 1 is a perspective view illustrating one embodiment of the dental anchor according to the present invention.

Referring now to the drawings, FIG. 1 shows a first embodiment of a dental anchor 10 according to the present invention. The dental anchor 10 is fabricated from a metal or an alloy, such as a precious metal or alloy of gold, silver or platinum, or a non-precious metal or alloy of stainless steel, chromium-nickel or cobalt-chromium, or like materials usable in the dental art.

Figure 3:
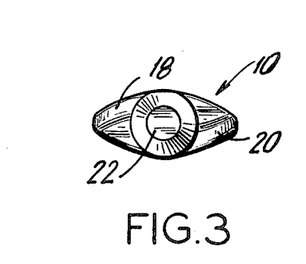
FIG. 3 is a top plane view of the dental anchor shown in FIG. 1.
Figure 6:
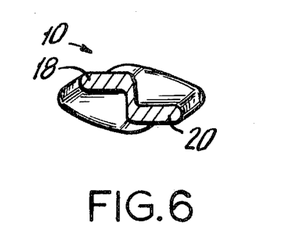
FIG. 6 is a cross-sectional view taken along line 6—6 of FIG. 1.

The dental anchor 10 includes a threaded section 12 and a manipulating end section 14 which are joined together by a frangible reduced thickness portion 16 so that the sections can be severed after being threaded into a channel in a tooth. The manipulating end section 14 includes a pair of projecting torque transferring wing portions 18, 20 extending outwardly in opposite directions therefrom at angles to the longitudinal axis of the dental anchor. These wing portions are formed by swedging or coining so that each wing portion has a thinner cross-section than the threaded section 12. As best shown in FIGS. 1 and 3, the wing portions 18, 20 are twisted relative to each other so that an upper part of wing portion 18 is disposed on an opposite side of the manipulating end section 14 than the upper part of wing portion 20. Accordingly, the lower parts of the wing portions are reversed, but the lower parts of the wing portions are still on opposite sides of the manipulating end section 14. This transition is clearly shown in FIGS. 6, 7 and 8.

Figure 7:
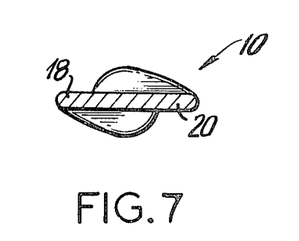
FIG. 7 is a cross-sectional view taken along line 7—7 of FIG. 1.
Figure 8:
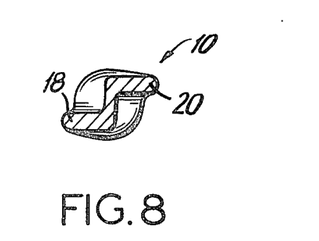
FIG. 8 is a cross-sectional view taken along line 8—8 of FIG. 1.

It is further noted, that each wing portion 18, 20 is provided with an arcuate longitudinal edge so that the wing portions are widest across their mid-sections or centers thereof, as clearly shown in FIG. 7. The purpose of the arcuate longitudinal edges will be set forth in more detail hereinafter below. It is noted that the free end 22 of the manipulating end section is preferably chamfered to aid in the insertion thereof into the shank which will also be discussed more fully hereinafter below.

Figure 2:
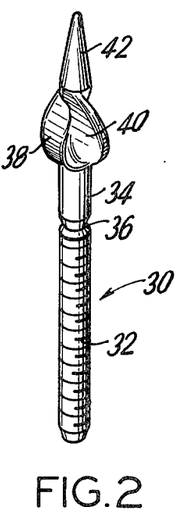
FIG. 2 is a perspective view illustrating an alternative embodiment of the dental anchor according to the present invention.

The dental anchor 30 shown in FIG. 2, is similar to the dental anchor 10 of FIG. 1, having a threaded section 32. A manipulating end section 34, a frangible portion 36 and wing portions 38, 40. However, the difference between these two pins is at the end of the manipulating end section, where the dental anchor 30 is provided with a conically shaped end 42. The conical end 42 functions as a pilot for guiding the manipulating end section 34 into the opening in the shank, as will be explained below.

Figure 4:
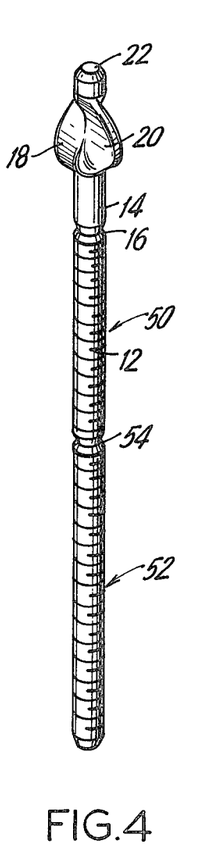
FIG. 4 is a perspective view illustrating a dental anchor similar to the dental anchor of FIG. 1, being provided with a second threaded section thereon.

The dental anchor 50 shown in FIG. 4 is also similar to the dental anchor 10 of FIG. 1, being provided with a threaded section 12, a manipulating end section 14, a frangible portion 16, wing portions 18, 20 and an end portion 22. However, dental anchor 50 is provided with a second threaded section 52 which is joined by a frangible portion 54 to the threaded section 12. It is noted, that the frangible portion 54 is of greater reduced thickness than the frangible portion 16 to provide a smaller cross-section in order to facilitate a greater tendency to fracture at the frangible portion 54. Thus, the dentist can first threadedly engage section 52 into the tooth, and sever the threaded section 12 therefrom in order that the threaded section 12 can be threaded into another channel.

Figure 5:
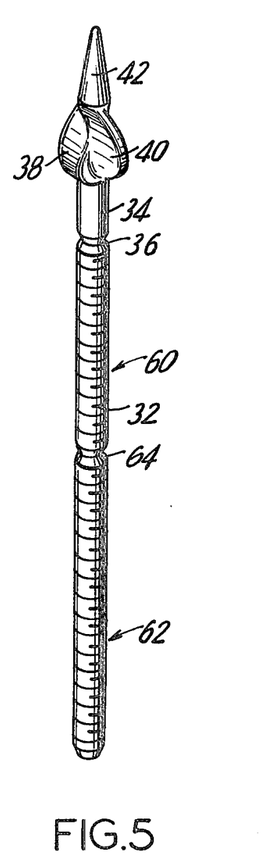
FIG. 5 is a perspective view illustrating a dental anchor similar to FIG. 2, being provided with a second threaded section thereon.

FIG. 5 discloses a dental anchor 60 similar to the dental anchor 30 of FIG. 2, having a threaded section 32, a manipulating end section 34, a frangible portion 36, wing portions 38, 40 and a conical end 42. However, as shown in connection with the dental anchor pin 50, the dental anchor pin 60 is provided with a second threaded section 62 joined by a frangible portion 64 to the threaded section 32, whereby the frangible portion 64 is of greater reduced thickness than the frangible reduced thickness portion 36 to provide a greater tendency to fracture at the frangible portion 64.

Figure 9:
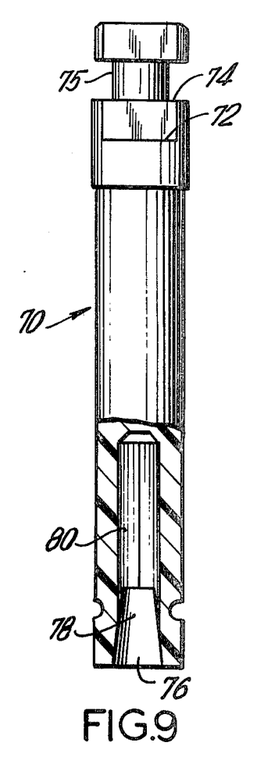
FIG. 9 is an elevational view, partly in section, illustrating the shank according to the present invention.
Figure 10:
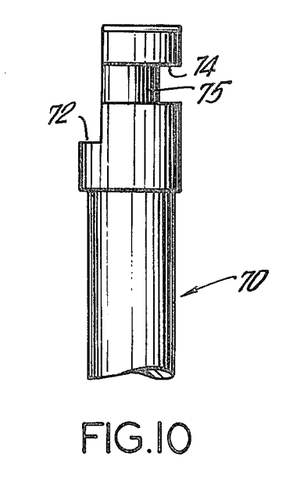
FIG. 10 is a side fragmentary elevational view of the shank of FIG. 9.

FIG. 9 shows the shank 70 of the present invention, the shank 70 being fabricated from a plastic material to provide flexibility and resiliency thereto. The upper end of the shank 70 is stepped to provide a recess 72 therein, as shown in FIG. 10. Additionally, a transverse groove 74 is provided in communication with the recess 72, defining a neck portion 75. The recess 72 and groove 74 of the shank 70 are structured to be received in a chuck of a conventional dental handpiece so that the shank 70 can be power driven in a conventional manner well known in the dental art. An additional function of the recess 72 and groove 74 will be set forth more fully hereinafter below.

Figure 11:
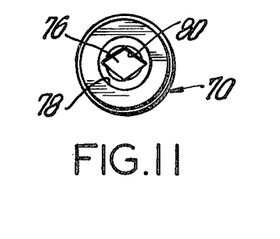
FIG. 11 is an end plane view of the shank of FIG. 9.

The opposite end of the shank 70 is provided with a centrally located longitudinally extending opening 76. The opening 76 has a tapered portion 78 leading therein from the end for guiding the manipulating end section of the dental anchor into the longitudinal opening 76. Additionally, an inner portion 80 as best shown in FIG. 11, has a diamond shape for receiving the wing portions of the manipulating end section of the dental anchor theein, to thereby restrict the rotation of the dental anchor.

Figure 12:
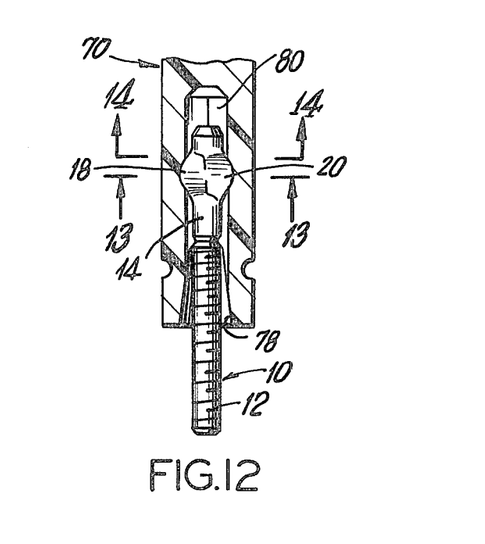
FIG. 12 is a fragmentary sectional view showing the dental pin within the shank.
Figure 13:
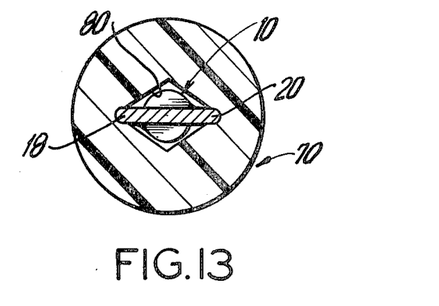
FIG. 13 is a sectional view taken along line 13—13 of FIG. 12.
Figure 14:
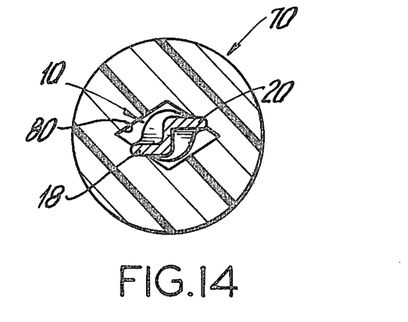
FIG. 14 is a sectional view taken along line 14—14 of FIG. 12.

As shown in FIGS. 12, 13 and 14, the manipulating end section 14 of the dental anchor 10 is guided into the opening 76 by the tapered portion 78, and then is force-fit into the diamond shaped portion 80 to its desired depth in the opening 76. The wing portions 18, 20 have a thicker dimension than that which can be accommodated by the diamond shaped portion 80. Thus, the wing portions 18, 20 bite into the sidewalls of the diamond shaped portion 80 to provide the force-fit as best shown in FIGS. 13 and 14. Thus, the manipulating end section 14 and therefore, the dental anchor 10, cannot rotate about its longitudinal axis with respect to the shank, where such rotation is restricted by the wing portions 18, 20. However, due to the arcuate shape of the wing portions, the dental anchor 10 can pivot relative to the shank 70, as will be described hereinafter below.

Figure 15:
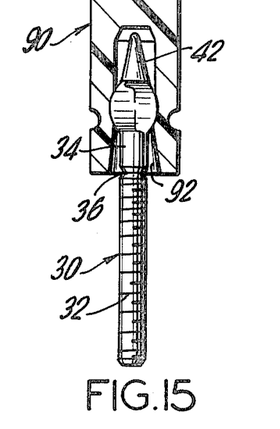
FIGS. 15 and 16 are fragmentary sectional views showing dental pins within associated shanks.

FIG. 15 discloses a shank 90 similar to shank 70 of FIG. 12, however, the length of the opening 92 therein has been shortened. Furthermore either of the shanks 70, 90 can receive any one of the dental anchors 10, 30, 50 or 60, where FIG. 15 shows dental anchor 30 disposed therein by way of example. The functional relationship between the shank 90 and the dental anchor 30 is the same as set forth, however the conical end 42 acts as a pilot for guiding the dental anchor 30 into the opening 92.

Figure 16:
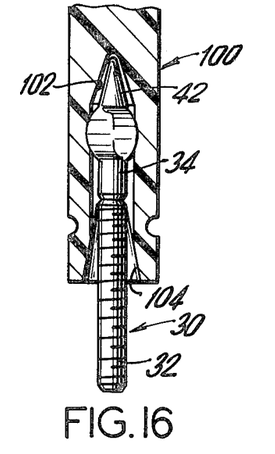

Preferably, as shown in FIG. 16, the shank 100 is similar to either the shank 70 or 90, however the shank 100 is provided with a conical portion 102 at the end of the longitudinal opening 104 in order to receive and position the conical end 42 of the dental anchor 30 for alignment thereof with the shank. It should be noted, that each of the shanks 70, 90 and 100 are fabricated from plastic and provided with an opening extending longitudinally therethrough which includes an initial tapered portion and an inner diamond shaped portion.

Figure 17:
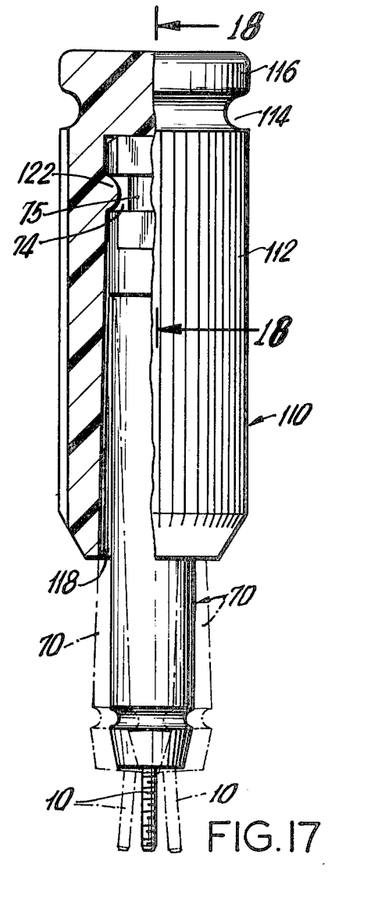
FIG. 17 is an elevational view, partly in section, showing the hand driver of the present invention receiving a shank and dental anchor assembly therein.

FIG. 17 discloses the hand driver 110 of the present invention, which is fabricated from a plastic material. A major portion of the outside surface of the hand driver is knurled at 112 in a longitudinal direction to aid in the hand rotation thereof. The upper end is provided with a transverse groove 114 and a smooth unknurled end 116. In use, the dentist preferably ties one end of a cord, such as dental floss, within the groove 114 and the other end of the cord or dental floss around his finger so that in case the hand driver 110, which is small in size, slips from his grip, the cord will prevent the hand driver 110 from falling down the patient's throat.

At the opposite end of the hand driver 110, an opening 118 extends longitudinally inwardly therefrom for receiving one of the above mentioned shanks therein, as shown in FIG. 17. The longitudinal opening 118 is tapered to facilitate the insertion of the shank.

Figure 18:
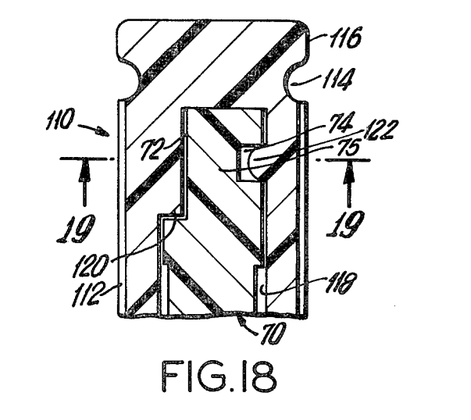
FIG. 18 is a cross-sectional view taken along line 18—18 of FIG. 17.
Figure 19:
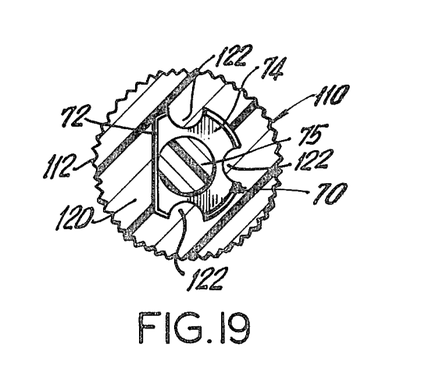
FIG. 19 is a cross-sectional view taken along line 19—19 of FIG. 18.

An inner end of the opening 118 is closed by an abutment portion 120. The abutment portion 120 is positioned to be received in the recess 72 of the shank 70 as shown in FIG. 18 so that rotating the hand driver 110 causes the shank 70 to also rotate. Additionally, projections or raised curved portions 122 extend into an inner portion of the opening 118. Accordingly, these projections are snapped into the groove 74 of the shank 70 to retain the shank 70 within the hand driver 110. As best shown in FIG. 19, preferably three projections 122 extend around the neck portion 75 of the shank 70. It is understood, that the above features also apply to the shanks 90 and 100, where each of these shanks have the same upper portion as shank 70.

As shown in FIG. 17, the curvature of the projections 122 permits a pivotal relationship between the shank 70 and the hand driver 110 as indicated in phantom lines. Accordingly, the tapering of the opening 118 also permits the pivotal movement between the shank and hand driver. Thus, the dentist is provided with both (1) the pivotal movement between the shank and the dental anchor and (2) the pivotal movement between the hand driver and the shank. A third pivotal movement is made possible by the plastic material of the shank, which permits a slight bending or flexure of the shank in order to obtain a proper alignment of the dental anchor and the channel.

Figure 20:
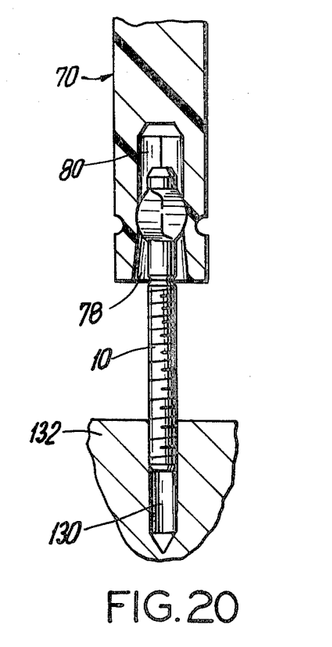
FIGS. 20-25 are fragmentary sectional views illustrating the pivotal relationship between the dental anchor and the shank as the dental anchor is being threaded into the channel in the tooth.
Figure 21:
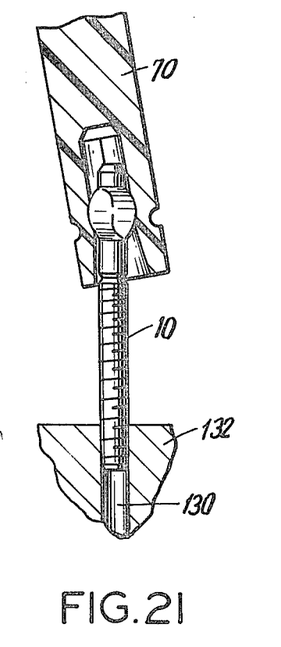
Figure 22:
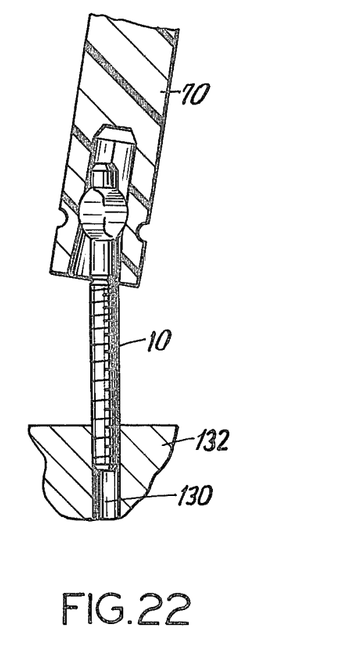

By way of example, FIGS. 20, 21 and 22 disclose the shank 70 holding the dental anchor 10 while being threaded into a channel 130 in a tooth 132. FIG. 20 discloses a straight alignment between the shank 70, the dental anchor 10 and channel 130. FIG. 21 discloses a pivotal arrangement with the shank 70 to one side and FIG. 22 discloses a pivotal arrangement with the shank 70 to the opposite side with the dental anchor 10 being in line with the channel 130, thereby allowing for proper alignment of the dental anchor with the channel.

Figure 23:
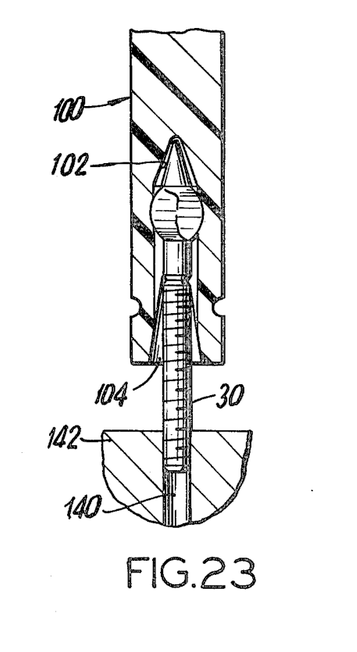
Figures 24, 25:
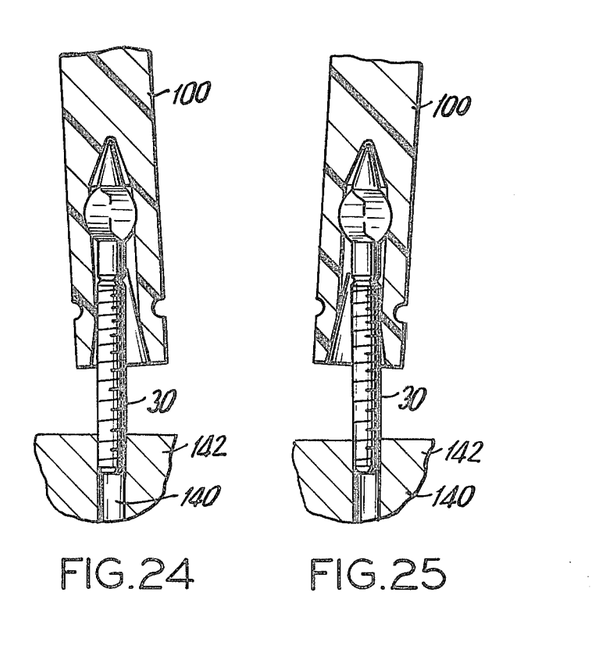

By a further way of example, FIGS. 23, 24 and 25 disclose the shank 100 holding the dental anchor 30 while being threaded into a channel 140 in a tooth 142. FIG. 23 discloses a straight alignment between the shank 100, the dental anchor 30 and channel 140. FIG. 24 discloses a pivotal arrangement with the shank 100 to one side and FIG. 25 discloses a pivotal arrangement with the shank 100 to the opposite side with the dental anchor 30 being in line with the channel 140, thereby allowing for proper alignment of the dental anchor with the channel.

Numerous alterations of the structure herein disclosed will suggest themselves to those skilled in the art. However, it is to be understood that the present disclosure relates to a preferred embodiment of the invention which is for purposes of illustration only and is not to be construed as a limitation of the invention.

What is claimed is:

1. A dental anchor comprising:
   at least one threaded section and one manipulating end section disposed along a longitudinal axis of said dental anchor and joined together by a frangible reduced thickness portion so that said sections can be severed after being threaded into a channel in a tooth;
   said manipulating end section including a pair of projecting torque transferring wing portions extending outwardly in opposite directions from said manipulating end section at angles to said longitudinal axis of said dental anchor;
   each wing portion having a thinner cross section than said threaded section;
   each wing portion extending longitudinally along said manipulating end section; and
   said wing portions being twisted relative to each other.

2. A dental anchor as claimed in claim 1, wherein a first part of one wing portion is disposed on one side of said manipulating end section and is adjacent to a first part of the other wing portion disposed on an opposite side of said manipulating end section; and a second part of said one wing portion is disposed on said opposite side and is adjacent to a second part of said other wing portion disposed on said one side.

3. A dental anchor as claimed in claim 1, wherein each of said wing portions has an arcuate longitudinal edge, said wing portions being widest across their centers.

4. A dental anchor comprising:
   at least one threaded section and one manipulating end section disposed along a longitudinal axis of said dental anchor and joined together by a frangible reduced thickness portion so that said sections can be severed after being threaded into a channel in a tooth;

said manipulating end section including a pair of projecting torque transferring wing portions extending outwardly in opposite directions from said manipulating end section at angles to said longitudinal axis of said dental anchor;

each wing portion having a thinner cross section than said threaded section;

each wing portion extending longitudinally along said manipulating end section; and said manipulating end section being provided with a conically shaped end remote from said threaded section.

5. A dental anchor as claimed in claim 4, wherein each of said wing portions has an arcuate longitudinal edge.

6. A dental anchor as claimed in claim 4, wherein a second threaded section is joined by a second frangible reduced thickness portion to said one threaded section, said second frangible reduced thickness portion being of greater reduced thickness than said first-mentioned frangible reduced thickness portion to provide a greater tendency to fracture.

7. A combination of a dental anchor and a shank for holding said dental anchor, said combination comprising:

said dental anchor including at least one threaded section and one manipulating end section disposed along a longitudinal axis of said dental anchor and joined together by a frangible reduced thickness portion so that said sections can be severed after being threaded into a channel in a tooth;

said shank including a longitudinal opening extending inwardly from one end thereof, said shank opening receiving at least said manipulating end section of said dental anchor in a force-fit connection therebetween;

said manipulating end section including torque transferring wing means for permitting said shank to pivot relative to said dental anchor when said dental anchor is being threaded into the channel in the tooth; and said shank opening having a tapered portion leading therein from said one end for guiding said manipulating end section into said longitudinal opening.

8. A combination as claimed in claim 7, wherein said shank is fabricated from a resilient and flexible plastic material to permit bending thereof for aligning said dental anchor with the channel.

9. A combination as claimed in claim 7, wherein at least an inner portion of said opening of said shank opening has a diamond shape for rotative restriction of said torque transferring wing means for said manipulating end section.

10. A combination of a dental anchor and a shank for holding said dental anchor, said combination comprising:

said dental anchor including at least one threaded section and one manipulating end section disposed along a longitudinal axis of said dental anchor and joined together by a frangible reduced thickness portion so that said sections can be severed after being threaded into a channel in a tooth;

said shank including a longitudinal opening extending inwardly from one end thereof, said shank opening receiving at least said manipulating end section of said dental anchor in a force-fit connection therebetween;

said manipulating end section including torque transferring wing means for permitting said shank to pivot relative to said dental anchor when said dental anchor is being threaded into the channel in the tooth;

said torque transferring wing means including a pair of projecting torque transferring wing portions extending outwardly in opposite directions from said manipulating end section at angles to said longitudinal axis of said dental anchor, each wing portion having a thinner cross section than said threaded section; and said wing portions being twisted relative to each other.

11. A dental anchor as claimed in claim 10, wherein a first part of one wing portion is disposed on one side of said manipulating end section and is adjacent to a first part of the other wing portion disposed on an opposite side of said manipulating end section; and a second part of said one wing portion is disposed on said opposite side and is adjacent to a second part of said other wing portion disposed on said one side.

12. A dental anchor as claimed in claim 10, wherein each of said wing portions has an arcuate longitudinal edge.

13. A combination of a dental anchor and a shank for holding said dental anchor, said combination comprising:

said dental anchor including at least one threaded section and one manipulating end section disposed along a longitudinal axis of said dental anchor and joined together by a frangible reduced thickness portion so that said sections can be severed after being threaded into a channel in a tooth;

said shank including a longitudinal opening extending inwardly from one end thereof, said shank opening receiving at least said manipulating end section of said dental anchor in a force-fit connection therebetween;

said manipulating end section including torque transferring wing means for permitting said shank to pivot relative to said dental anchor when said dental anchor is being threaded into the channel in the tooth;

said torque transferring wing means including a pair of projecting torque transferring wing portions extending outwardly in opposite directions from said manipulating end section at angles to said longitudinal axis of said dental anchor, each wing portion having a thinner cross section than said threaded section; and said manipulating end section being provided with a conically shaped end remote from said threaded section.

14. A combination as claimed in claim 13, wherein an inner end portion of said longitudinal opening of said shank has a conical shape receiving said conically shaped end of said manipulating end section for alignment between said shank and said dental anchor.

15. A combination as claimed in claim 13, wherein a second threaded section is joined by a second frangible reduced thickness portion to said one threaded section, said second frangible reduced thickness portion being of greater reduced thickness than said first-mentioned frangible reduced thickness portion to provide a greater tendency to fracture.

16. A combination of a dental anchor, a shank holding said dental anchor, and a hand driver holding and turning said shank, said combination comprising:

said dental anchor including at least one threaded section and one manipulating end section disposed along a longitudinal axis of said dental anchor and joined together by a frangible reduced thickness portion so that said sections can be severed after being threaded into a channel in a tooth;

said shank including a longitudinal opening extending inwardly from one end thereof, said shank opening receiving at least said manipulating end section therein;

said hand driver including an opening extending inwardly from one end thereof, said hand driver receiving an opposite end of said shank therein, said hand driver including first means for rotating said shank and second means for releasably retaining said shank within said hand driver with said second means permitting a pivotal relationship between said shank and said hand driver when said dental anchor is being threaded into the channel in the tooth; and said hand driver being fabricated from a plastic material.

17. A combination as claimed in claim 16, wherein said opposite end of said shank is stepped to provide a recess, said first means of said hand driver including an abutment portion disposed at an inner end of said opening of said hand driver, said abutment portion being disposed in said recess of said shank for rotating said shank.

18. A combination as claimed in claim 16, wherein an outside surface of said hand driver is knurled in a longitudinal direction to aid in rotating said hand driver.

19. A combination as claimed in claim 16, wherein said opposite end of said shank is provided with a transverse groove, said second means of said hand driver including projections extending into an inner portion of said opening of said hand driver, said projections being snapped into said groove of said shank to retain said shank while permitting pivotal movement therebetween.

20. A combination as claimed in claim 19, wherein said opening of said hand driver has a tapered portion leading therein from said one end thereof for guiding said shank into said hand driver opening and for permitting said pivotal movement.

21. A combination as claimed in claim 16, wherein said manipulating end section of said dental anchor includes torque transferring wing means for permitting said shank to pivot relative to said dental anchor when said dental anchor is being threaded into the channel in the tooth.

22. A combination as claimed in claim 21, wherein said shank is fabricated from a resilient and flexible plastic material to permit bending thereof for aligning said dental anchor with the channel.

23. A combination as claimed in claim 21, wherein said torque transferring wing means includes a pair of projecting torque transferring wing portions extending outwardly in opposite directions from said manipulating end section at angles to said longitudinal axis of said dental anchor, each wing portion having a thinner cross section than said threaded section, each wing portion extending longitudinally along said manipulating end section.

24. A combination of a dental anchor and a shank holding said dental anchor, said combination comprising:

said dental anchor including at least one threaded section and one manipulating end section disposed along a longitudinal axis of said dental anchor and joined together by a frangible reduced thickness portion so that said sections can be severed after being threaded into a channel in a tooth;

said shank including a longitudinal opening extending inwardly from one end thereof, said shank opening receiving at least said manipulating end section of said dental anchor in a force-fit connection therebetween;

said manipulating end section including torque transferring wing means for permitting said shank to pivot relative to said dental anchor when said dental anchor is being threaded into the channel in the tooth;

said torque transferring wing means includes a pair of projecting torque transferring wing portions extending outwardly in opposite directions from said manipulating end section at angles to said longitudinal axis of said dental anchor, each wing portion having a thinner cross section than said threaded section;

said shank being fabricated from resilient and flexible means to permit bending thereof for aligning said dental anchor with the channel, said resilient and flexible means being a plastic material;

each of said wing portions having a longitudinal edge, each wing portion edge being engaged in sidewalls of said shank opening to provide both said force-fit connection and the pivotal relationship between said shank and said dental anchor.

25. A combination as claimed in claim 24, wherein at least an inner portion of said shank opening has a diamond shape for rotative restriction of said torque transferring wing means of said manipulating end section.

26. A combination as claimed in claim 24, wherein said longitudinal edges of said wing portions are arcuate.

27. A combination as claimed in claim 24, wherein a second threaded section is joined by a second frangible reduced thickness portion of said one threaded section, said second frangible reduced thickness portion being of greater reduced thickness than said first-mentioned frangible reduced thickness portion to provide a greater tendency to fracture.

28. A combination of a dental tool and a hand driver holding and turning said dental tool, said combination comprising:

said dental tool including a shank section at one end;

said hand driver including an opening extending inwardly from one end thereof, said hand driver opening receiving said shank section of said dental tool therein, said hand driver including first means for rotating said shank section and second means for releasably retaining said shank section within said hand driver with said second means permitting a pivotal relationship between said dental tool and said hand driver;

said hand driver being fabricated from a plastic material;

said shank section being provided with a traverse groove, said second means of said hand driver including projections extending into an inner portion of said opening of said hand driver, said projections being snapped into said groove of said shank section to retain said dental tool while permitting pivotal movement therebetween; and said shank section being stepped to provide a recess, said first means of said hand driver including an abutment portion disposed at an inner end of said opening of said hand driver, said abutment portion being disposed in said recess of said shank section for rotating said dental tool.

29. A combination as claimed in claim 28, wherein an outside surface of said hand driver is knurled in a longitudinal direction to aid in rotating said hand driver.

30. A combination as claimed in claim 28, wherein said opening of said hand driver has a tapered portion leading therein from said one end thereof for guiding said shank section into said hand driver opening and for permitting the pivotal movement therebetween.

* * * * *